(12) United States Patent
Le

(10) Patent No.: US 8,387,444 B2
(45) Date of Patent: Mar. 5, 2013

(54) METHOD OF MODELING STEAM GENERATOR AND PROCESSING STEAM GENERATOR TUBE DATA OF NUCLEAR POWER PLANT

(75) Inventor: Qui V. Le, Pittsburgh, PA (US)

(73) Assignee: Westinghouse Electric Company LLC, Cranberry Township, PA (US)

(*) Notice: Subject to any disclaimer, the term of this patent is extended or adjusted under 35 U.S.C. 154(b) by 642 days.

(21) Appl. No.: 12/760,148

(22) Filed: Apr. 14, 2010

(65) Prior Publication Data

US 2011/0172980 A1 Jul. 14, 2011

Related U.S. Application Data

(60) Provisional application No. 61/260,448, filed on Nov. 12, 2009.

(51) Int. Cl.
*G01M 19/00* (2006.01)
(52) U.S. Cl. ................................................ 73/112.02
(58) Field of Classification Search ............... 73/112.01, 73/112.02
See application file for complete search history.

(56) References Cited

U.S. PATENT DOCUMENTS

| 4,341,113 | A | 7/1982 | Gutzwiller, Jr. |
| 4,942,545 | A | 7/1990 | Sapia |
| 5,023,549 | A | 6/1991 | Dau et al. |
| 6,114,849 | A | 9/2000 | Price et al. |
| 6,959,267 | B2 * | 10/2005 | Le .................... 702/189 |
| 7,637,653 | B2 * | 12/2009 | Pop et al. .............. 374/7 |
| 7,810,991 | B2 * | 10/2010 | Pop et al. .............. 374/7 |
| 2005/0154564 | A1 * | 7/2005 | Le .................... 702/189 |
| 2009/0292574 | A1 * | 11/2009 | Pop et al. ................ 705/8 |
| 2011/0172964 | A1 * | 7/2011 | Le .................... 702/183 |

OTHER PUBLICATIONS

Xiang et al, Automated Analysis of Rotating Probe Multi-Frequency Eddy Curernt Data from Steam Generator Tubes, International Journal of Applied Electromagnetics and Mechanics. 12(2000) IOS Press. pp. 151-164 retrieved from the internet (Dec. 12, 2010): url/ <http://users.rowan.edu/-polikar/Research/Publications/ijaem00.pdf>.

* cited by examiner

*Primary Examiner* — Eric S McCall

(57) ABSTRACT

An improved method of inspecting the tubes of a steam generator of a nuclear reactor involves modeling the steam generator and comparing signals of a tube from an eddy current sensor with aspects of the model to determine whether further analysis is required. The model can advantageously include exception data with regard to particular regions of interest (ROIs) of particular tubes that is based upon historic data collected from the steam generator.

12 Claims, 3 Drawing Sheets

METHOD OF MODELING STEAM GENERATOR AND PROCESSING STEAM GENERATOR TUBE DATA OF NUCLEAR POWER PLANT

CROSS REFERENCE TO RELATED APPLICATION

This application is related to and claims priority from provisional application Ser. No. 61/260,448, filed Nov. 12, 2009, entitled "Real Time Automated Analysis (RTAA) of Steam Generator Tubing Inspection".

BACKGROUND OF THE INVENTION

1. Field

The invention relates generally to nuclear power plants and, more particularly, to a method of evaluating the tubes of a steam generator of a nuclear power plant.

2. Description of the Related Art

Nuclear power plants are generally well known. Nuclear power plants can generally be stated as comprising a reactor that includes one or more fuel cells, a primary loop that cools the reactor, and a secondary loop that drives a steam turbine which operates an electrical generator. Such nuclear power plants typically additionally include a heat exchanger between the primary and secondary loops. The heat exchanger typically is in the form of a steam generator which comprises tubes that carry the primary coolant and a plenum that carries the secondary coolant in heat-exchange relationship with the tubes and thus with the primary coolant.

As is also generally known, the tubes of a steam generator are subject to wear from mechanical vibration, corrosion, and other mechanisms. It thus is necessary to periodically inspect the tubes of a steam generator for wear in order to avoid failure of a tube which might result in nuclear contamination of the secondary loop, by way of example. While numerous methodologies have been employed for performing such inspection, such methodologies have not been without limitation.

One method of inspecting the tubes of a steam generator involves the insertion of an eddy current sensor into one or more of the tubes and to receive from the eddy current sensor a signal which typically is in the form of a voltage and a phase angle. An analyst reviewing the signal data typically must possess a high degree of expertise in order to accurately ascertain from the signal data the current condition of the tubes of the steam generator. A typical steam generator might possess between three thousand and twelve thousand tubes, by way of example, with each tube being several hundred inches in length. Thus, the review of eddy current data can require the expenditure of large amounts of time by an analyst. While certain testing protocols may require the testing of fewer than all of the tubes of a steam generator, depending upon the particular protocol, the time in service, and other factors, the analysis of such data still requires significant time and expense.

Among the difficulties involved in the analysis of eddy current data is the determination of whether a signal is indicative of a possible failure of a portion of a tube or whether the signal is not indicative of such a failure. Each tube of a steam generator typically has a number of bends and a number of mechanical supports. In passing an eddy current sensor through such a tube, the signal from the eddy current sensor will vary with each mechanical support and with each bend, and the signal also will vary in the presence of a flaw such as a crack or a dent in the tube. As such, the difficulty in analysis involves the ability to determine whether a change in a signal from an eddy current is indicative of a known geometric aspect of a tube such as a bend or support, in which case further analysis of the signal typically is unnecessary, or whether the change in signal from the eddy current sensor is indicative of a crack or a dent, in which case further analysis of the signal typically is necessary.

Existing methodologies for analyzing tube signals have involved the use of one or more pre-established signal thresholds. However, due to the great variability of tube geometries within a given steam generator and the differing actual condition of each such tube, the use of a limited number of fixed signal thresholds to interpret eddy current signal data from the tubes still results in many portions of many tube signals exceeding the limited number of fixed signal thresholds and therefore requiring further manual examination by an analyst. It thus would be desirable to provide an improved system for assessing a current condition of the tubes of a steam generator.

SUMMARY OF THE INVENTION

Accordingly, an aspect of the invention can include providing an improved system for modeling a steam generator that includes both baseline parameters of one or more regions of interest (ROIs) and that further includes exception data for individual ROIs of individual tubes based upon historic analysis of the tubes. The historic analysis of the tubes may have been conducted at the time of manufacture of the steam generator or during a prior in-service inspection. During the collection of such historic data, eddy current data for each tube of a steam generator can be collected and evaluated for quality assurance. Data for a particular ROI of a particular tube that exceeds what otherwise would be the baseline performance of the ROI can be stored as exception data. Such exception data relates to particular ROIs that have been determined to generate signal data that would exceed what would be the corresponding baseline signal parameters but that is still acceptable because it is indicative of a historic aspect of the ROI rather than being indicative of a flaw in the ROI. Once the tube data has been collected, a model of the steam generator can be created that includes both baseline performance parameters for a large variety of ROIs and that can further include the aforementioned exception data.

During testing of a steam generator, a signal from an eddy current sensor is input into a location algorithm to identify an actual physical ROI of the tube under analysis and to also identify an exemplary ROI in the model of the steam generator. If the signal from the eddy current sensor with respect to the physical ROI exceeds the baseline parameters of the corresponding exemplary ROI, the need for additional analysis is triggered. Initially, the additional analysis involves accessing the exception data to determine whether exception data exists for the particular physical ROI of the particular tube that is under analysis with the eddy current sensor. If such exception data exists, the historic exception data is compared with the current signal of the physical ROI from the eddy current sensor, and the need for still further analysis is triggered only if the current signal exceeds the historic exception data by a predetermined threshold. Also, if no corresponding exception data exists for the current physical ROI, the need for further analysis is likewise triggered. However, if the eddy current sensor data for a given ROI does not exceed the baseline parameters of the corresponding exemplary ROI from the model, or if the signal from the given physical ROI fails to exceed the exception data for that ROI by a predetermined threshold, no action is taken as to that particular ROI, meaning that the ROI is considered to PASS, and no further evaluation by an analyst is required.

The collection of data can additionally involve the collection and storage of data for each tube at its transition with a tube sheet, both at the hot leg and the cold leg of the tube. Due to the thickness of the tube sheet in relation to the thicknesses of the tubes themselves and the other support structures, baseline signals cannot be reliably established for all tube sheet transitions. As such, tube sheet transition eddy current data is collected and stored for each leg of each tube of a steam generator at the time of manufacture or at an in-service inspection. During subsequent testing of the steam generator tubes, the historic signal from any given tube sheet transition can be compared with and effectively subtracted from the current signal from the same tube sheet transition in order to generate a new signal that is indicative of a change in the tube sheet transition and that is generally free of historic signal artifacts. The resultant signal can then be amplified in order to magnify the change in condition of the tube for simplified evaluation by an analyst or otherwise.

Accordingly, an aspect of the invention is to provide one or more improved methodologies that reduce the effort required to analyze the tubes of a steam generator of a nuclear power plant.

Another aspect of the invention is to provide a system that improves the accuracy of evaluating the current condition of the tubes of a steam generator of a nuclear power plant by requiring less manual evaluation by an analyst, thereby avoiding fatigue of the analyst and improved overall results with respect to ROIs that are in genuine need of evaluation by an analyst.

These and other aspects of the invention can be generally described as relating to an improved method of non-destructively assessing a current condition of a number of tubes of a steam generator of a nuclear power plant, the general nature of which can be stated as including establishing a model of the steam generator that comprises a set of baseline parameters for each of a plurality of exemplary regions of interest (ROIs) of a number of the tubes of the steam generator, extracting a signal from each of a number of physical ROIs of a number of the tubes, comparing the signal from a given physical ROI of a tube with the set of baseline parameters of the corresponding exemplary ROI of the model, and triggering additional processing when at least a portion of the signal from the given physical ROI exceeds at least a portion of the set of baseline parameters of the corresponding exemplary ROI.

BRIEF DESCRIPTION OF THE DRAWINGS

A further understanding of the invention can be gained from the following Detailed Description when read in conjunction with the accompanying drawings in which.

Similar numerals refer to similar parts throughout the specification.

DETAILED DESCRIPTION

Figure 1:
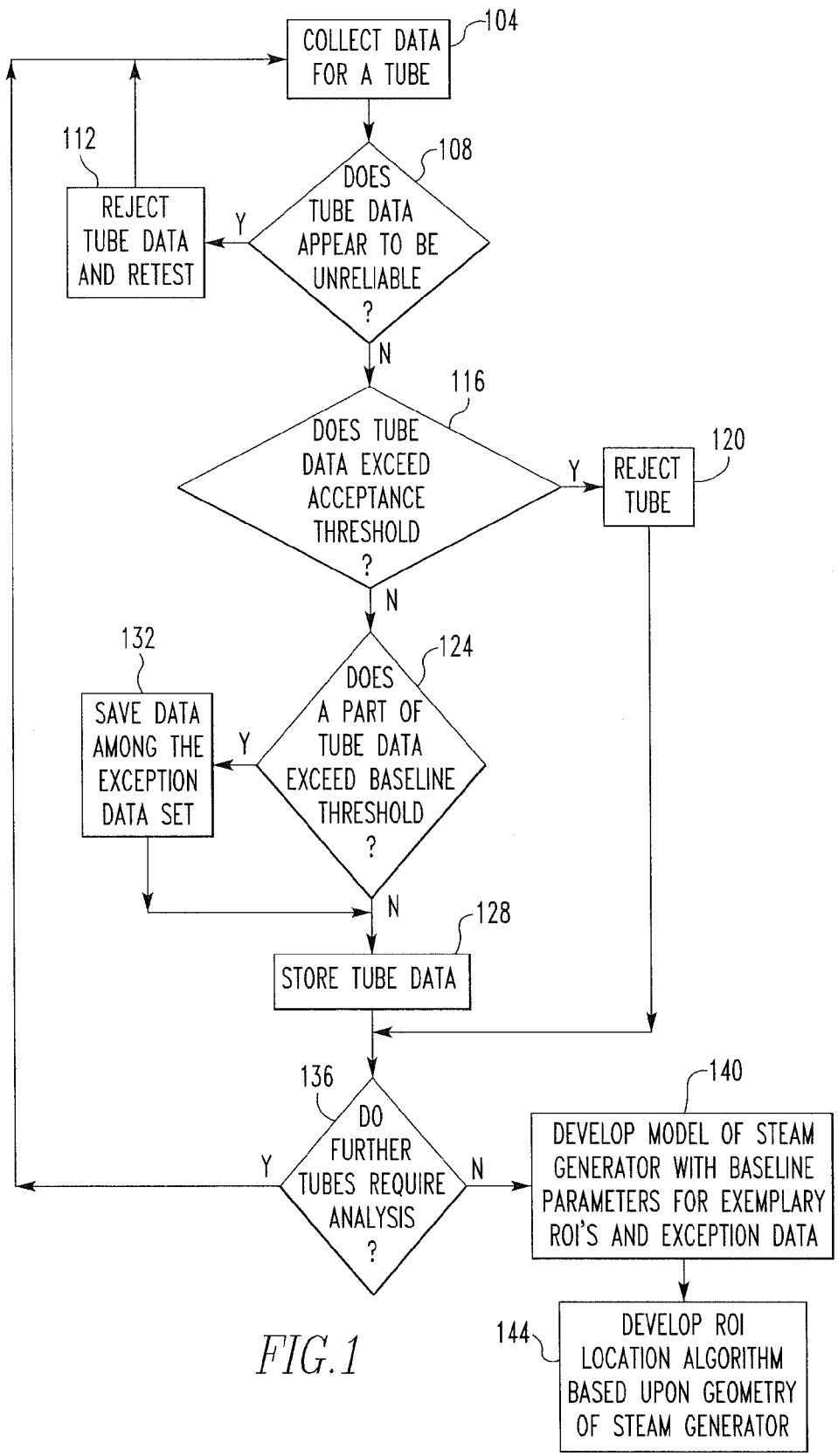
FIG. 1 is a flowchart depicting certain aspects of the invention.
Figure 2:
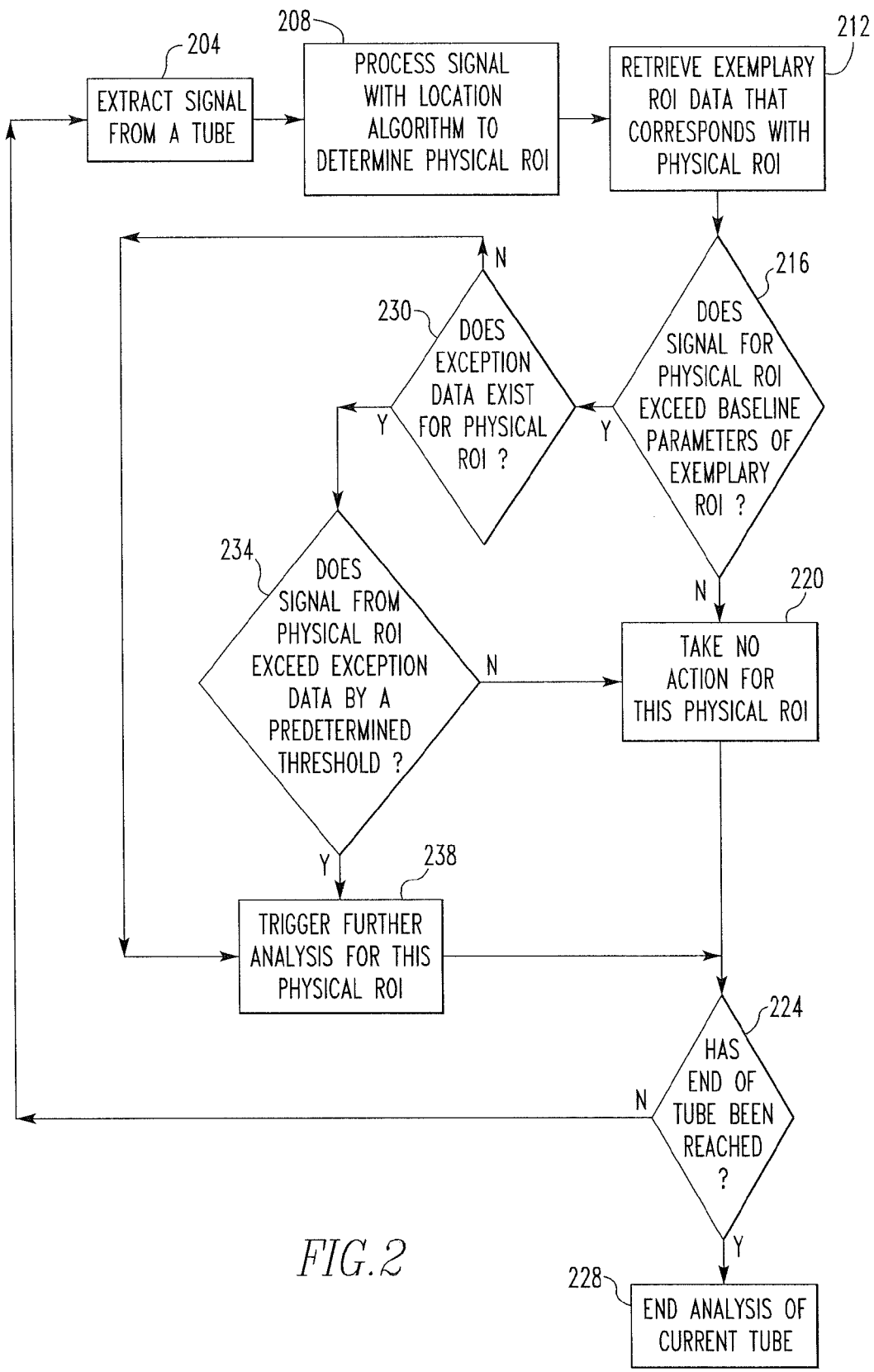
FIG. 2 is a flowchart depicting certain other aspects of the invention.
Figure 3:
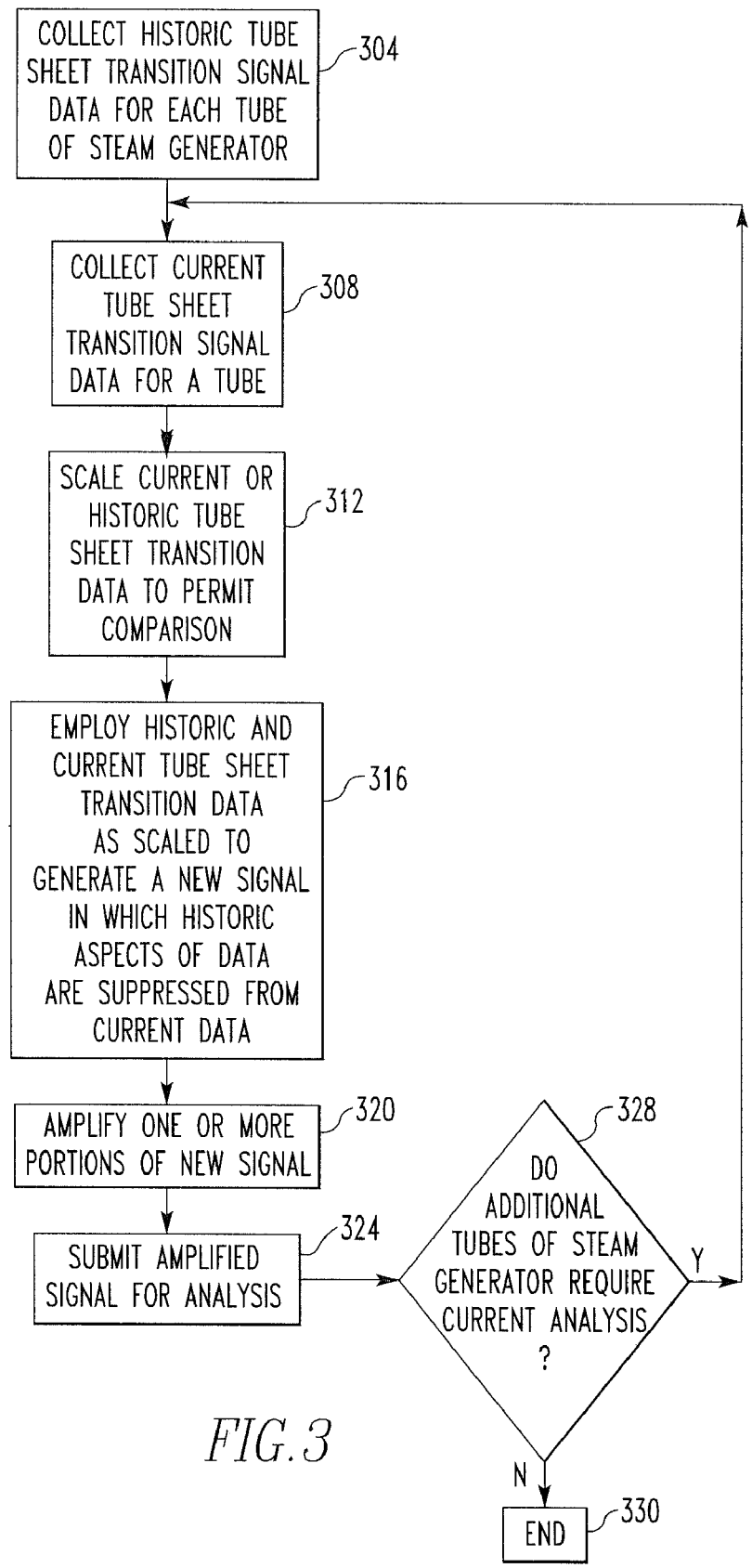
FIG. 3 is another flowchart depicting certain other aspects of the invention.

Improved methods in accordance with the invention are depicted in general terms in FIGS. 1-3. The methods generally all relate to nuclear power plants and, more particularly, the inspection of tubes of a steam generator of a nuclear power plant. The various methodologies discussed herein can be employed in whole or in part in any combination without departing from the present concept.

Certain aspects of the methodologies employed herein involve the collection of data with the use of an eddy current sensor that is received within the interior of an elongated tube of a steam generator and that is passed through the interior of the tube along the longitudinal extent thereof. Longitudinal movement of the sensor can be performed manually, although it can also advantageously be performed by a robotically-controlled advancement mechanism that advances the eddy current sensor at a controlled rate and that is capable of providing a data stream component representative of the longitudinal distance of the eddy current sensor along the tube at any given time. Other data streams from the eddy current sensor typically comprise a voltage component that characterizes an amplitude and another component that characterizes a phase angle. Although many methodologies can be employed for the storage and analysis of such data streams, one methodology involves the storage of voltage and phase data at given points along the longitudinal length of a tube. Typically, thirty data points per inch are collected and stored, but other data distributions and densities can be employed without departing from the present concept.

As is generally understood, a typical steam generator includes a plenum that encloses perhaps four thousand to twelve thousand individual tubes that each comprise a hot leg and a cold leg that pass through a tube sheet, which is itself a slab of metal that is typically twenty or more inches thick. Each tube may be several hundred inches long and have either a single U-bend or a pair of elbow bends, although other geometries can be employed without departing from the present concept. Each such tube typically additionally includes twenty to thirty physical supports of differing geometries. During initial manufacture, the hot and cold legs of each tube are assembled to the tube sheet by receiving the two ends of the tube in a pair of holes drilled through the tube sheet and by hydraulically bulging the ends of the tube into engagement with the cylindrical walls of the drilled holes.

While the geometry of each tube of a steam generator typically is different from nearly every other tube of the steam generator, the overall construction of the steam generator enables generalizations to be made with regard to the geometry of the tubes as a whole. That is, each tube can be said to include a pair of tube sheet transitions at the ends thereof which typically are characterized by an eddy current sensor voltage on the order of thirty (30.0) volts. Between the two tube sheet transitions are various straight runs, supports, and bends. The typical eddy current voltage for a straight section of tube is 0.05 volts, and the typical voltage for a bend of a tube is 0.1 volts. A typical voltage for a support may be 0.2 volts, but various types of supports can exist within a given steam generator, all of which may produce different characteristic voltages.

Advantageously, however, the various arrangements of straight sections, supports, and bends as a function of distance along a tube are of a limited number of permutations within any given steam generator. As such, a location algorithm is advantageously developed from the known geometry of the steam generator and the historic data that can be collected from the steam generator, wherein an input to the algorithm of a series of voltage and distance values can identify a particular region of interest (ROI) of a tube that is under analysis. That is, the wear that is experienced by a tube often can occur at a tube sheet transition, at a location of attachment of a tube to a mechanical support, at a transition between a straight section and a bend in a tube, or at other well understood locations. The various segments of a given tube can be divided into various regions of interest (ROIs) which can be identified during data collection with a high degree of accuracy based upon the details of the steam generator geometry that are incorporated into the location algorithm. As such, by inputting voltage, phase, and distance data into the location algorithm, the location algorithm can identify a specific segment and thus physical ROI of the tube being analyzed.

The invention can also be said to include the development of a model for the steam generator that includes baseline parameters such as voltage and phase for each of a plurality of exemplary ROIs that exist in the particular steam generator. Advantageously, and as will be set forth in greater detail below, the model additionally includes exception data for particular ROIs of particular tubes that have voltage and/or phase angle parameters that would exceed the baseline parameters of the corresponding ROI of the model but that are nevertheless acceptable, i.e., the signals from such ROIs are not themselves indicative of flaws that require further evaluation by an analyst.

The baseline parameters for the various exemplary ROIs of the model can be established in any of a variety of ways. In the exemplary embodiment described herein, the various baseline parameters for the various exemplary ROIs of the model are established based upon theoretical evaluation of tubes and their ROIs, as well as experimental data based upon eddy current analysis of actual tubes and their physical ROIs. The direct physical analysis of tubes such as through the collection of eddy current data of individual tubes of a steam generator advantageously enables the collection of data with respect to typical ROIs that can be employed in establishing baseline parameters for exemplary ROIs of the model. Such direct physical analysis of tubes can additionally be employed to collect data that is later stored as exception data for particular ROIs of particular tubes.

Additionally and advantageously, such direct collection of eddy current data during the initial manufacture of a steam generator can enable an initial evaluation of each tube to assess whether the tube should be rejected or whether the data appears to be unreliable and should be recollected. A tube may be rejected if the data suggests that it is defective in manufacture. On the other hand, the data may need to be recollected if it appears that the eddy current sensor was functioning improperly or if other data collection aspects appear to be erroneous or unreliable.

FIG. 1 generally depicts an exemplary methodology for the collection of tube data which enables the development of a model of a steam generator and the development of a location algorithm that is based upon the geometry of the steam generator. Processing begins, as at 104, where eddy current data is collected for a given tube of the steam generator. As mentioned elsewhere herein, the data stream typically will include components of voltage, phase, and distance, all of which can be detected as a continuous signal or as a discrete set of data points along the length of the tube. The insertion of the eddy current sensor into the tube and the longitudinal progression of the eddy current sensor along its longitudinal length can be performed manually or can advantageously be performed by a specially configured robot.

Processing continues, as at 108, where it is determined whether the data derived from the eddy current sensor signal is potentially unreliable. For instance, if the data suggests a possible data collection error, processing continues as at 112, where the tube data is rejected, and the tube is retested. Processing thereafter would continue, as at 104. However, if at 108 the data is not determined to be unreliable, processing continues, as at 116, where it is determined whether the tube data derived from the eddy current signal exceeds an acceptance threshold, such as would indicate that the tube itself is mechanically or otherwise defective. In the event that the data exceeds an acceptance threshold, the tube is rejected, as at 120.

If the tube data does not exceed the acceptance threshold at 116, processing continues, as at 124, where it is determined whether any portions of the tube data exceed what should theoretically be the baseline parameters of that portion of the tube, i.e., the baseline parameters for the corresponding exemplary ROI of the model of the steam generator. By way of example, it may be determined that the physical ROI of the tube that is under analysis includes a physical support and the eddy current sensor is indicating a voltage of 0.4 volts. While an analyst may determine that the voltage that would typically be expected for such an ROI is 0.2 volts, the analyst may nevertheless determine that the particular physical ROI is acceptable and that the voltage of 0.4 volts is an acceptable anomaly. In such a circumstance, the data for the particular ROI for this particular tube will be saved, as at 132, as a portion of an exception data set. In this regard, it is reiterated that the tube or its data would already have been rejected, as at 112 or 120 respectively, if the data for the aforementioned ROI suggested that the ROI would be unacceptable.

Processing continues from both 124 and 132 onward to 128 where the tube data is stored in a data set. It is then determined, as at 136, whether further tubes require eddy current analysis as set forth above. If further tubes await testing, processing continues, as at 104, with a new tube. Otherwise, processing continues, as at 140, where the model of the steam generator is developed with a set of baseline parameters for each of a plurality of exemplary ROIs. The model further includes the aforementioned exception data for one or more particular ROIs of one or more particular tubes. It is understood that the inclusion as at 140 of the development of the steam generator model at this particular location within the exemplary methodology is intended to be merely an example of a point at which a model of the steam generator can be developed. It is understood that with analytical methods, at least an initial model of the steam generator can be developed, with the experimental collection of tube data from 104 through 132 being supplied to the model to provide refinement of the model and to provide exception data. It thus is understood that the model of the steam generator can be developed in whole or in part at any time depending upon the data and the analysis that are available.

Processing continues to 144 where the location algorithm which identifies various ROIs can be developed based upon the geometry of the steam generator and other factors. As was mentioned elsewhere herein with respect to the development of the model of the steam generator, the location algorithm can likewise be developed in whole or in part at any time depending upon the analytical and experimental data that is available in the development process depicted generally in FIG. 1. When completed, the location algorithm advantageously can receive a data stream from an eddy current sensor within the tube of the steam generator and can employ the voltage, phase, and distance data components to identify any of a variety of exemplary ROIs that are stored within the model of the steam generator. That is, the location algorithm can employ the eddy current signal within a tube of the steam generator to identify a particular segment of the tube and thus a physical ROI of the tube, and the location algorithm can additionally identify from the model that was developed of the steam generator a corresponding exemplary ROI and its baseline parameters for comparison with the eddy current signal that is being collected from the physical ROI.

The testing of the tubes of a steam generator is depicted in an exemplary fashion in FIG. 2. It is understood that the operations depicted generally in FIG. 1 typically will occur at a first time and will be in the nature of a historic data set. The operations occurring in FIG. 2 typically occur at a second, subsequent time and may more likely be directed toward current or present testing of a steam generator. Processing begins, as at 204, where a signal is extracted from a tube of the steam generator. The signal from the eddy current sensor is processed with the aforementioned location algorithm, as at 208, to determine the physical ROI that is the source of the signal that is being collected from the tube under analysis. The location algorithm then employs, as at 212, the signal from the eddy current sensor to retrieve from the model an exemplary ROI that is determined to correspond with the physical ROI that has been located by the location algorithm. It is then determined, as at 216, whether the signal data for the physical ROI exceeds the baseline parameters of the exemplary ROI from the model that was identified and retrieved at 212. If it is determined at 216 that the eddy current signal for the physical ROI does not exceed the baseline parameters of the exemplary ROI, processing will continue, as at 220, where no further action will be taken with respect to this particular physical ROI. That is, no additional analysis will be triggered for this particular physical ROI, thereby avoiding the need for an analyst to perform any evaluation with respect to this physical ROI.

It is then determined, as at 224, whether the end of the tube under analysis has been reached. If so, the analysis of the current tube ends, as at 228. Another tube can then be analyzed. However, if the end of the tube is determined at 224 to not be reached, processing continues, as at 204, where the eddy current signal is continued to be extracted from the tube under analysis.

The aforementioned baseline parameters of the various exemplary ROIs of the model can be developed in any of a variety of fashions. Most typically, the baseline parameters will be developed with the use of theoretical data and experimental data, as suggested above. For instance, the typical eddy current voltage that one might expect to detect from a straight section of a tube is 0.05 volts, and the data collection effort depicted generally in FIG. 1 might demonstrate, by way of example, that the tested voltage values for each straight segment of each tube is 0.08 volts or less. As such, the baseline voltage for an exemplary ROI that corresponds with a straight section of a tube might be established 0.1 volts. This would enable all physical ROIs that are straight sections of tubes to, in their original condition, not exceed the baseline parameter of 0.1 volts and thus not trigger the need for further analysis, as at 220.

Similarly, the typical eddy current sensor voltage that one might expect from a curved section of a tube is 0.1 volts, and the baseline parameter for experimental ROIs of bend segments of each tube might be established at 0.2 volts. Physical supports typically generate an eddy current voltage of 0.2 volts, so the baseline parameter for a physical support ROI might be established at 0.3 volts. Such baseline parameters typically will be based upon the various specifications of the steam generator and the nuclear power plant, along with theoretical and experimental data regarding the steam generator. It is understood, however, that the baseline parameters typically will be selected such that an eddy current sensor signal that exceeds a baseline parameter is worthy of further evaluation by an analyst, assuming that applicable exception data for the particular physical ROI does not already exist in the model. That is, the baseline parameters desirably will be selected such that no further action is triggered when the eddy current sensor signals are below that which should reasonably trigger further analysis of the particular physical ROI. It is understood, however, that various methodologies may be employed for establishing the baseline parameters of the exemplary ROIs without departing from the present concept.

It is also noted that the baseline parameters can include voltages, phase angles, pattern data, and any other type of characterization of an exemplary ROI that may be appropriate. The degree of sophistication of the baseline parameters is limited only by the ability to collect and analyze data regarding the tubes. As such, the baseline parameters of an exemplary ROI can be determined to be exceeded if any one or more of the various parameters in any combination are exceeded by a signal without limitation. Additionally or alternatively, the baseline parameters could have an even greater degree of sophistication wherein certain combinations of parameters need to be exceeded in a certain fashion for the system to trigger the need for further analysis, by way of example.

On the other hand, if it is determined, as at 216, that the signal for the physical ROI exceeds in some fashion the baseline parameters of the identified corresponding exemplary ROI, processing continues, as at 230, where it is determined whether exception data exists for the physical ROI that is under analysis. As mentioned elsewhere herein, the exception data advantageously will be a part of the model of the steam generator. If such exception data is determined at 230 to exist, processing continues, as at 234, where it is determined whether the signal from the physical ROI exceeds the exception data by a predetermined threshold. That is, it is not expected that the physical ROI that is the subject of the exception data will remain unchanged during the life of the steam generator, and rather it is expected that the physical ROI might degrade over time due to wear, corrosion, etc. Since the physical ROI has already been determined at the time of taking the historic data set to have a signal which exceeds the baseline parameters that would otherwise be expected from a similar ROI, the threshold that is already built into the baseline parameters is unlikely to be useful in evaluating the particular physical ROI that is the subject of the retrieved exception data. As such, a separate threshold is established based upon various factors which, if exceeded by the present signal from the physical ROI, will trigger further analysis as at 238, of this particular physical ROI. Such further analysis likely will be manual evaluation by an analyst. On the other hand, if it is determined at 234 that the signal from the physical ROI fails to exceed the retrieved exception data by the predetermined threshold, processing continues, as at 220, where no further action is taken for this particular physical ROI. Further evaluation by an analyst is also triggered, as at 238, if it is determined, as at 230, that no exception data exists for this particular physical ROI.

It is noted that an additional notification can be triggered if the baseline parameters of the exemplary ROI are exceeded by a significant amount, or if the predetermined threshold for the exception data is exceeded by a significant amount, in order to alert an analyst that an increased level of attention should be directed to a particular physical ROI, for example. In the exemplary embodiment depicted herein, for instance, further analysis is triggered if either the baseline parameters of the exemplary ROI or the predetermined threshold of the exception data is exceeded in any fashion. However, an additional notification can be generated if the signal exceeds the baseline parameters or the predetermined threshold of the exception data by 25%, by way of example. It is understood that any type of criteria can be employed to trigger such heightened further analysis.

It therefore can be seen that the eddy current data that is collected from a tube under analysis is evaluated using the model that includes exemplary ROIs with baseline performance parameters and further includes exception data for ROIs of particular tubes, with the result being the triggering of further analysis such as evaluation by an analyst only in specific predefined circumstances such as would occur at 238. As such, the manual evaluation effort that is required of an analyst using the exemplary methods set forth herein is greatly reduced compared with known methodologies.

It is noted that the exemplary method depicted generally in FIG. 2 envisions a real-time automated analysis system wherein a signal that is collected from a tube is input directly into the location algorithm and is evaluated as it is collected. It is understood, however, that different methodologies may be employed. For instance, the data from one or more tubes can be collected and stored and then evaluated as a whole rather than being analyzed on a real-time basis. Other variations can be envisioned that are within the scope of the present concept.

Due to the thickness of the tube sheet, as mentioned elsewhere herein, the eddy current data that is collected from a tube in the tube sheet transition region typically is of a voltage far in excess of any of the baseline parameters of any of the exemplary ROIs. Moreover, the variation in eddy current voltage from one tube sheet transition to another is also far in excess of any baseline parameter of an exemplary ROI. For instance, and has been mentioned elsewhere herein, the eddy current voltage for a tube sheet transition might be on the order of thirty (30.0) volts. The eddy current voltage of another tube sheet transition might be 25.0 volts, and that of another tube might be 35.0 volts. Since the eddy current voltages at tube sheet transitions are one or more orders of magnitude greater than any voltage that would be generated in other portions of the tube, i.e., portions other than the tube sheet transition, an improved method is depicted in FIG. 3 and is described herein for facilitating the analysis of signals collected from tube sheet transitions of a steam generator that is undergoing analysis.

In general terms, it is understood that the eddy current signals from tubes in the tube sheet transition area of a steam generator are of a voltage that is sufficiently high that the portion of the eddy current signal which might indicate a possible flaw, i.e., the signal of interest, which might be on the order of 0.1 volts, is far too small in comparison with the overall eddy current signal to be easily detected or evaluated. As such, another aspect of the invention is to collect historic tube sheet transition signal data for each tube of a steam generator, as at 304, and employ the historic tube sheet transition data for use at a later time in comparison with tubes of a steam generator that is under analysis after a period of use. Advantageously, the historic data shares certain aspects with currently collected data, and the method advantageously suppresses from the current signal any aspects that were also present in the historic tube sheet transition data in order to generate an improved simpler signal that is indicative of a change in condition of the tube sheet transition area of a tube under analysis. The historic tube sheet transition signal data can be taken at the time of manufacture of the steam generator or can be taken at a later time, such as during an in-service inspection of a steam generator.

The historic tube sheet transition signal data that is collected at 304 during manufacture or in-service inspection of a steam generator is then stored for future retrieval and comparison with subsequently collected data during a current testing operation. That is, current tube sheet transition signal data is collected, as at 308, for a given tube of a steam generator. The historic tube sheet transition data for the same tube is retrieved. It is typically the case that some type of scaling with respect to either the current data or the historic data will occur, as at 312, to permit comparison. By way of example, it may be necessary to reduce or increase or otherwise manipulate all of the values of either the current or historic data sets since different eddy current sensors or other instrumentation were employed to take both sets of data or because of other differing operating parameters between the eddy current sensors employed to take the historic and the current tube sheet transition data. Other types of scaling may be necessary if the data points of the historic tube sheet transition data do not match perfectly with the data points of the current tube sheet transition data. As mentioned elsewhere herein, data may be taken at thirty locations per inch, although forty-five locations per inch may likewise be employed, as can other data signal densities. Still other scaling may be required if the direction of movement of the eddy current sensor is different between the historic data and the current data. For example, the historic data may have been based upon longitudinal movement of an eddy current sensor in a direction from the tube sheet toward the tube sheet transition, whereas the current data may involve an eddy current sensor that is moving in a direction from the tube sheet transition toward the tube sheet. Regardless of the nature of the historic and current tube sheet transition data, scaling or other mathematical manipulations may be performed at 312 to permit comparison between the two.

The current tube sheet transition data and the historic tube sheet transition data, as may be scaled at 312, are then employed to generate a new signal, as at 316. The new signal is simpler than either the historic or the current tube sheet transition data signals since the historic aspects of the data, as are indicated with the historic tube sheet transition data, are suppressed from the currently collected data signal. The new signal is representative of the change in condition of the tube sheet transition that is under analysis between the time at which the historic tube sheet data transition was collected, such as at the time of manufacture or during an in-service inspection, and the time at which the current tube sheet transition data has been collected.

Moreover, it may be desirable to amplify, as at 320, one or more portions of the new signal that is generated, as at 316. Such an amplified signal would emphasize those aspects of the new signal that would be even more indicative of a change in the condition of the tube sheet transition between the time the historic data was collected and the time that the current data is collected.

The amplified signal is then submitted, as at 324, for analysis. Such analysis might be performed automatically or may be performed manually by an analyst. It is then determined, as at 328, whether any additional tubes of the steam generator require analysis with respect to their tube sheet transition region. If further tubes require analysis, processing continues, as at 308. Otherwise, processing ends, as at 330.

In this regard, it is understood that the aforementioned tube sheet transition analysis can be performed as a part of the analysis depicted generally in FIG. 2 or can be performed separately. In this regard, the historic tube sheet transition data that was collected at 304 potentially can be saved as part of the model of the steam generator, particularly as a special part of the exception data set. As such, it may be possible to completely analyze a tube from one tube sheet transition through its longitudinal extent and to its opposite tube sheet transition using the teachings herein. As mentioned elsewhere herein, however, it is possible to analyze the tube sheet transitions separately from the other portions of the tubes, as may be desired.

It is also noted that the teachings employed herein can be applied in a cumulative fashion to permit multiple sets of historic data to be compared with current data. That is, historic data can be taken at a first time, such as at the time of manufacture of a steam generator or at an in-service inspection, and such historic data can be employed during a subsequent evaluation of the steam generator tubes. The data that is developed during such a subsequent evaluation may then be stored as a second historic data set. Both historic data sets can then be compared with data that is collected during a further inspection of the steam generator to enable the change in the condition of various tubes to be charted as a function of time over the course of several inspections that occur at several different times. Other uses of the data can be envisioned.

It is understood that the analysis described herein can be performed on a digital computer or other processor of a type that is generally known. For instance, such a computer might include a processor and a memory, with the memory having stored therein one or more routines which can be executed on the processor. The memory can be any of a wide variety of machine readable storage media such as RAM, ROM, EPROM, EEPROM, FLASH, and the like without limitation. The signal from the eddy current sensor might be received by an analog-to-digital converter which provides a digital input to the computer for processing and storage of the signals. The historic and current data can be stored on any such storage media and can potentially be transported or transmitted for use on other computers or processors as needed.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes that come within the meaning and range of equivalency of the claims are to be embraced within their scope.

What is claimed is:

1. A method of non-destructively assessing a current condition of a number of tubes of a steam generator of a nuclear power plant, the method comprising:
   establishing a model of the steam generator that comprises a set of baseline parameters for each of a plurality of exemplary regions of interest (ROIs) of a number of the tubes of the steam generator;
   extracting a signal from each of a number of physical ROIs of a number of the tubes;
   comparing the signal from a given physical ROI of a tube with the set of baseline parameters of the corresponding exemplary ROI of the model; and
   triggering additional processing when at least a portion of the signal from the given physical ROI exceeds at least a portion of the set of baseline parameters of the corresponding exemplary ROI.

2. The method of claim 1 wherein the model further comprises an exception data set for each of one or more physical ROIs of each of one or more tubes of the number of tubes, each exception data set being representative of a preexisting signal of the physical ROI that exceeds the set of baseline parameters of the corresponding exemplary ROI, and wherein the triggering of additional processing comprises seeking in the model an exception data set for the given physical ROI.

3. The method of claim 2, further comprising:
   identifying an exception data set for the given physical ROI;
   comparing the exception data set for the given physical ROI with the signal from the given physical ROI; and
   triggering the need for still further processing if at least a portion of the signal from the given physical ROI exceeds at least a portion of the exception data set for the given physical ROI.

4. The method of claim 3, further comprising refraining from the triggering of still further processing with respect to the given physical ROI when no portion of the signal from the given physical ROI exceeds by a predetermined threshold the exception data set for the given physical ROI.

5. The method of claim 1 wherein the extracting of a signal from each of a number of the physical ROIs of a number of the tubes further comprises, for each such tube:
   detecting a signal from the tube;
   subjecting at least a portion of the signal from the tube to an algorithm identify at least a first physical ROI of the tube and to identify a corresponding exemplary ROI of the model.

6. The method of claim 5 wherein the detecting of the signal from the tube comprises detecting a signal component that is indicative of one or more distances along the tube and detecting one or more signal components that are each indicative of a support structure for the tube.

7. The method of claim 1, further comprising:
   at the time of manufacture of the steam generator, subjecting each of at least some of the tubes to an initial data quality evaluation; and
   responsive to a determination that at least a portion of the data of a particular tube exceeds a predetermined signal threshold, rejecting at least one of:
   the data of the particular tube, and
   the particular tube itself.

8. The method of claim 1, further comprising:
   at the time of manufacture of the steam generator, subjecting each of at least some of the tubes to an initial data quality evaluation; and
   responsive to a determination that at least a portion of the data of a particular tube is likely to be unreliable, rejecting at least one of:
   the data of the particular tube, and
   the particular tube itself.

9. The method of claim 1, further comprising refraining from the triggering of additional processing with respect to a particular physical ROI when no portion of a signal from the particular physical ROI exceeds a set of baseline parameters of a corresponding exemplary ROI.

10. The method of claim 1, further comprising triggering an additional notification if the at least portion of the signal from the given physical ROI exceeds the at least portion of the set of baseline parameters of the corresponding exemplary ROI by a predetermined amount.

11. The method of claim 1 wherein the set of baseline parameters for at least a first exemplary ROI include a plurality of characteristic characteristics that comprise one or more of a voltage, a phase angle, and a pattern, and further comprising determining that the at least portion of the signal from the given physical ROI exceeds the at least portion of the set of baseline parameters of the corresponding exemplary ROI when any one or more of the plurality of characteristics is exceeded.

12. A machine readable storage medium having stored thereon instructions which, when executed on a processor of a computing device, cause the computing device to perform the operations of claim 1.

* * * * *